United States Patent [19]

Watmough

[11] Patent Number: 4,600,011
[45] Date of Patent: Jul. 15, 1986

[54] TELE-DIAPHANOGRAPHY APPARATUS

[75] Inventor: David J. Watmough, Aboyne, United Kingdom

[73] Assignee: The University Court of The University of Aberdeen, Aberdeen, Scotland

[21] Appl. No.: 547,500

[22] Filed: Nov. 1, 1983

[30] Foreign Application Priority Data

Nov. 3, 1982 [GB] United Kingdom ............... 8231404

[51] Int. Cl.$^4$ .............................................. A61B 6/12
[52] U.S. Cl. ..................... 128/664; 128/665; 128/396
[58] Field of Search ............ 128/664, 665, 396, 6

[56] References Cited

U.S. PATENT DOCUMENTS

| | | | |
|---|---|---|---|
| 2,098,990 | 11/1937 | Newton | 128/396 |
| 2,867,209 | 1/1959 | Foures et al. | |
| 3,335,716 | 8/1967 | Alt et al. | 128/664 |
| 3,674,008 | 7/1972 | Johnson | 128/665 |
| 3,798,366 | 3/1974 | Hunt et al. | 128/664 |
| 3,806,633 | 4/1974 | Coleman | |
| 3,971,954 | 7/1976 | Kleinberg et al. | |
| 4,213,462 | 7/1980 | Sato | |
| 4,267,844 | 5/1981 | Yamanishi | 128/665 |
| 4,286,602 | 9/1981 | Guy | 128/665 |
| 4,298,005 | 11/1981 | Mutzhas | 128/396 |
| 4,312,357 | 1/1982 | Andersson et al. | 128/665 |
| 4,336,809 | 6/1982 | Clark | 128/665 |
| 4,350,150 | 9/1982 | Kubota et al. | 128/6 |
| 4,444,190 | 4/1984 | Mutzhas | 128/396 |
| 4,467,812 | 8/1984 | Stoller | 128/665 |
| 4,479,499 | 10/1984 | Alfano | 128/665 |

FOREIGN PATENT DOCUMENTS

| | | |
|---|---|---|
| 0075800 | 4/1983 | Italy . |
| 2068537 | 8/1981 | United Kingdom . |
| 2092856A | 8/1982 | United Kingdom . |
| 2111794A | 7/1983 | United Kingdom . |

OTHER PUBLICATIONS

Edrich et al, Focussing Long-Wave Thermography, 14th Microwave Power Symposium, Jun. 1979, pp. 266-267.

Primary Examiner—Kyle L. Howell
Assistant Examiner—Ruth S. Smith
Attorney, Agent, or Firm—Birch, Stewart, Kolasch & Birch

[57] ABSTRACT

A tele-diaphanography apparatus suitable for transilluminating human or animal tissues, which apparatus comprises a first housing including a source of light of wavelength from 300 Nm to 2000 Nm; means for directing light from the first light source onto the tissues to be examined by transillumination, and a heat-absorbing filter located in the path of the light from the light source; a second housing including a source of light of wavelength from 300 Nm to 2000 Nm, and means for directing the light from the second light source onto the tissues to be examined; a light detector for detecting the light transmitted through the transilluminated tissue being examined; a visual display unit for displaying the image detected by the light detector; and recording means for recording the image detected by the light detector.

18 Claims, 3 Drawing Figures

TELE-DIAPHANOGRAPHY APPARATUS

BACKGROUND OF THE INVENTION

1. Field of the Invention

The present invention relates to tele-diaphanography apparatus, that is to say apparatus suitable for examining human or animal tissues by transillumination thereof for the primary purpose of locating tumors, whether malignant or benign.

2. Description of the Related Art

The detection of tumors at an early stage of their development is particularly desirable as it frequently enables the tumors to be removed from the patient so as to prevent the tumorous condition from spreading to other parts of the body. This is particularly true of cancerous tumors of the female breast.

Breast-screening of women to detect cancerous tumors is now commonplace, but current diagnostic methods and apparatus all have disadvantages. The most common diagnostic methods are palpation and X-ray mammography. Palpation is a relatively subjective method and is therefore somewhat unrealiable, while X-ray mammography, though very reliable, carries a slight risk of inducing cancer owing to the X-ray irradiation used in the examination. A further diagnostic method in which renewed interest has been shown recently is diaphanography. This method relies on transilluminating the brest tissue using visible or infra-red light and recording the resultant image. Such transillumination techniques have the attraction that the non-ionising radiation which passes through the brest tissues carries no risk of inducing brest cancer. A method and apparatus utilising such a system is described in my co-pending British Patent Application No. 2092856A.

When using the diagnostic method and apparatus of British Patent Application No. 2092856A it is usual as a first stage of the examination to perform a visual examination of the brest by placing the light source housing beneath the breast and inspecting the superior surface of the breast to detect the presence of any shadows (indicative of neoplasms) and areas of increased brightness (indicative of cysts). Thereafter, as a second stage in the examination, a record of the transilluminated image is made, for example by using an infra-red television camera to produce a color coded image which can be stored on video-tape or by photograping the image displayed on a visual display unit.

However, we have found that in performing such a visual examination the housing surrounding the light source which is placed beneath the breast can get very hot and subsequent application of the hot housing to a patient when producing a permanent record of the transilluminated image can cause the patient considerable discomfort. The present invention aims to overcome this disadvantage.

SUMMARY OF THE INVENTION

According to a first aspect of the present invention there is provided a tele-diaphanography apparatus suitable for transilluminating human or animal tissues, which apparatus comprises a first housing including a source of light of wavelength from 300 Nm to 2000 Nm; means for directing light from the first light source onto the tissues to be examined by transillumination, and a heat-absorbing filter located in the path of the light from the light source; a second housing including a source of light of wavelength from 300 Nm to 2000 Nm, and means for directing the light from the second light source onto the tissues to be examined; a light detector for detecting the light transmitted through the transilluminated tissue being examined; a visual display unit for displaying the image detected by the light detector; and recording means for recording the image detected by the light detector.

According to the above-mentioned arrangement, the telediaphanography apparatus includes a first housing for performing the required visual examination of the breast tissues and which includes a heat-absorbing filter which allows a light source in the housing to be placed near the skin of the patient but avoids over-heating of the skin and tissues to be examined, and in addition a second light source used to produce a recorded image of the breast tissue.

In an alternative arrangement, instead of using two separate light sources, it is possible to use a single light source in a housing which is adapted selectively to receive alternative endpieces one of which incorporates a heat-absorbing filter. Accordingly, in a second embodiment, the present invention provides a tele-diaphanography apparatus suitable for transilluminating human or animal tissues, which apparatus includes a single housing including a source of light of wavelength from 300 Nm to 2000 Nm, the housing being selectively engageable with either a first means for directing light onto the tissues to be examined, or a second means for directing light onto the tissues to be examined, which first means includes a heat-absorbing filter located in the path of the light from the light source; a light detector, for detecting the light transmitted through the transilluminated tissue being examined; a visual display unit for displaying the image detected by the light detector; and recording means for recording the image detected by the light detector.

BRIEF DESCRIPTION OF THE DRAWINGS

The present invention will now be described, by way of example only, with reference to the accompanying drawings, in which.

DETAILED DESCRIPTION

Figure 1:
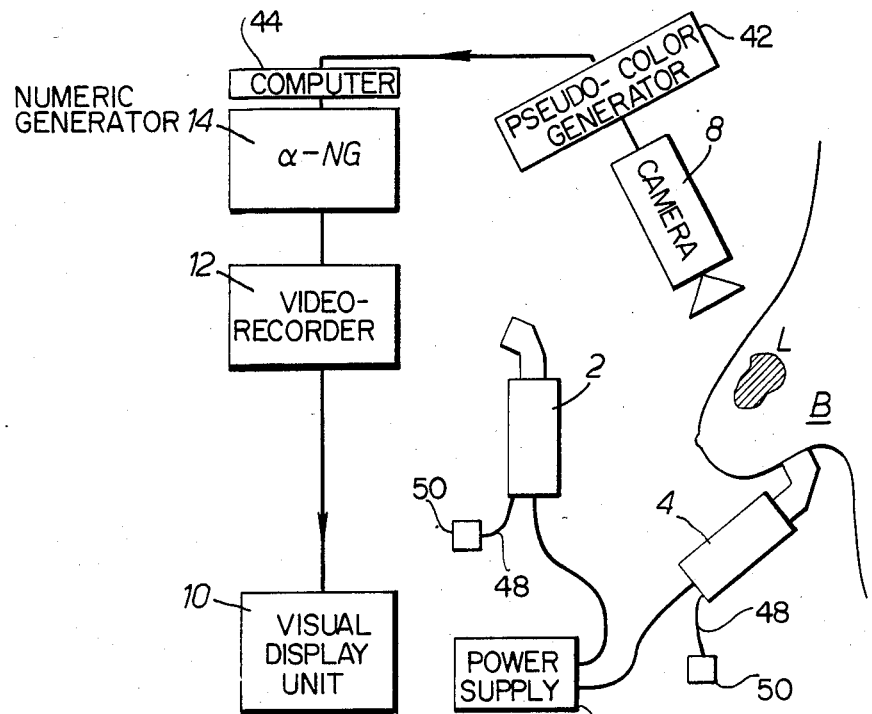
FIG. 1 is a schematic representation of an apparatus in accordance with the first aspect of the present invention.
Figure 2:
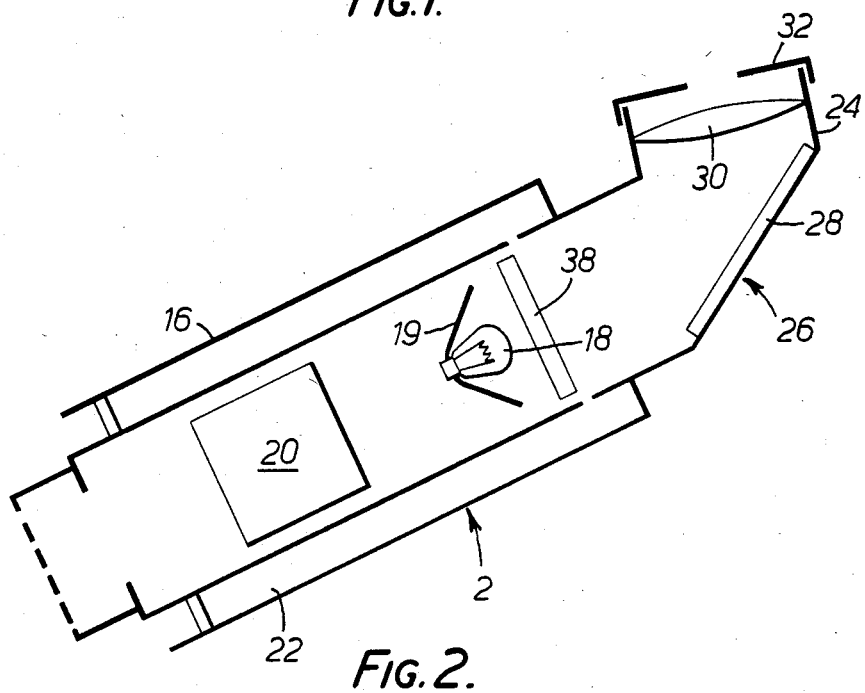
FIG. 2 is a diagrammatic section of an elevation of a housing suitable for performing a visual examination when using the apparatus of FIG. 1.

Referring to FIGS. 1 and 2 of the drawings, there is shown a tele-diaphanography apparatus particularly adapted for the examination of female breasts and intended to be used in the mass screening of women for breast cancer. The apparatus includes a first housing 2 used for the transillumination of breast tissue (B) when performing an initial visual examination of a patient's breasts, and a second housing 4 used for subsequently transilluminating the breast tissue to obtain an image from which a permanent record is to be made.

In both housings 2 and 4, controlled from a power supply 6, a non-ionising form of radiation, such as light from a tungsten filament bulb, is used as a light source.

In the initial visual examination, the outer end of extension 24 of housing 2, (shown in more detail in FIG. 2) is applied to the underside of the breast which is being examined. Some of the light from the light source is absorbed and scattered by the breast tissue but much of the light in the red and near infra-red region of the electromagnetic spectrum is transmitted by the breast tissue. As a result, an image of the interior of the breast showing lesions (L) even down to 8 mm diameter or less can be seen on the upper surface of the breast.

Since breasts vary in size and thickness, the light source in the housing must of necessity be relatively powerful; consequently it dissipates considerable heat. However, by incorporating a heat-absorbing filter 38 in housing 2, the housing will remain cool for at least 5-10 minutes, which time is sufficient to perform the required visual examination of the patient's breasts. The heat-absorbing filter 38 absorbs the infra-red radiation issuing from the light source and thereby prevents the temperature of the angled extension 24 of the housing 2 from rising to a level which is uncomfortable for the patient when the housing is applied to her skin.

After the visual examination has been concluded and a lesion has been located, the first light source is switched off and the second light source is used in the same manner as the first light source to obtain a further image of the lesion on the upper surface of the breast. The second housing is in most respects the same as housing 2 except that it does not include the heat-absorbing filter 38. However, housing 4 will remain cool for 2 to 3 minutes, which time is sufficient for the operator of the apparatus to make the desired images without discomfort to the patient.

The images are recorded by means of a camera 8 which is sensitive to red and near infra-red radiation. Usually an infra-red sensitive television camera is used, and the images recorded by the camera are projected on a visual display unit 10. When a suitabe image has been generated, the image is recorded, for example on a video-recorder 12, or by taking a photograph of the image projected on the visual display unit 10.

In addition, if desired, details concerning the patient can be incorporated in the image by providing an α-numeric generator 14 and associated keyboard which enables the operator to key in the required data for projection on the visual display unit 10.

Furthermore, to assist in the interpretation of the generated image, it may be advantageous to generate a colored image in accordance with a pre-selected colour scale from the image recorded by the television camera. Thus, it may be advantageous to include a pseudo-colour generator 42 which will generate a coloured image from the output of the television camera.

The construction of the first housing 2 is shown in more detail in FIG. 2. As will be seen, the housing comprises a cylindrical casing 16 within which is located a light source 18, typically a tungsten filament bulb, and a relector 19. The bulb and associated parts are cooled by a fan 20 which draws air from outside the housing along channels 22 into the interior of the housing over the bulb 18. The fan 20 may, in an alternative construction, not be present in the housing itself, but may instead be incorporated in a separate unit 50 to which the or each housing is connected by a flexible conduit 48.

The outer end of the housing carries an angled extension 24 for facilitating the application of the light beam to the underside of the patients' breast. This extension includes at its elbow 26, a mirror 28 for deflecting the beam of light emanating from the bulb 18 out through the free end of the extension 24. This free end of the extension may carry a lens 30 and a variable diaphragm 32 for obtaining optimal resolution of the tumours within the breast tissues. The initial visual examination with the housing which contains the heat absorbing filter is usually carried out with the variable diaphragm fully open so as to permit the maximum amount of light to pass through the breast so as to enable the operator to see any lesions which are present irrespective of their size. When the breast is illuminated with the housing without the heat absorbing filter, the aperture is usually reduced so as to reduce the amount of light passing through the breast. It has been found that small lesions tend to scatter light when too much light passes through the breast. The scatter tends to mask the small lesions and prevent them from being imaged. Thus, the variable aperture enables optimal visual examination and imaging of a variety of sizes of lesions.

In order to prevent the temperature of the angled extension 24 from rising rapidly to a level which will be uncomfortable to the skin of the patient undergoing the examination, the housing 2 includes a heat-absorbing filter 38, suitably of glass, located in the cylindrical casing 16 in the path of the light beam issuing from the light source 18. The presence of the filter ensures that the angled extension 24 will remain suitably cool for at least 5-10 minutes which time is sufficient for the operator of the tele-diaphanography apparatus to perform his visual examination of the patient's breasts.

Figure 3:
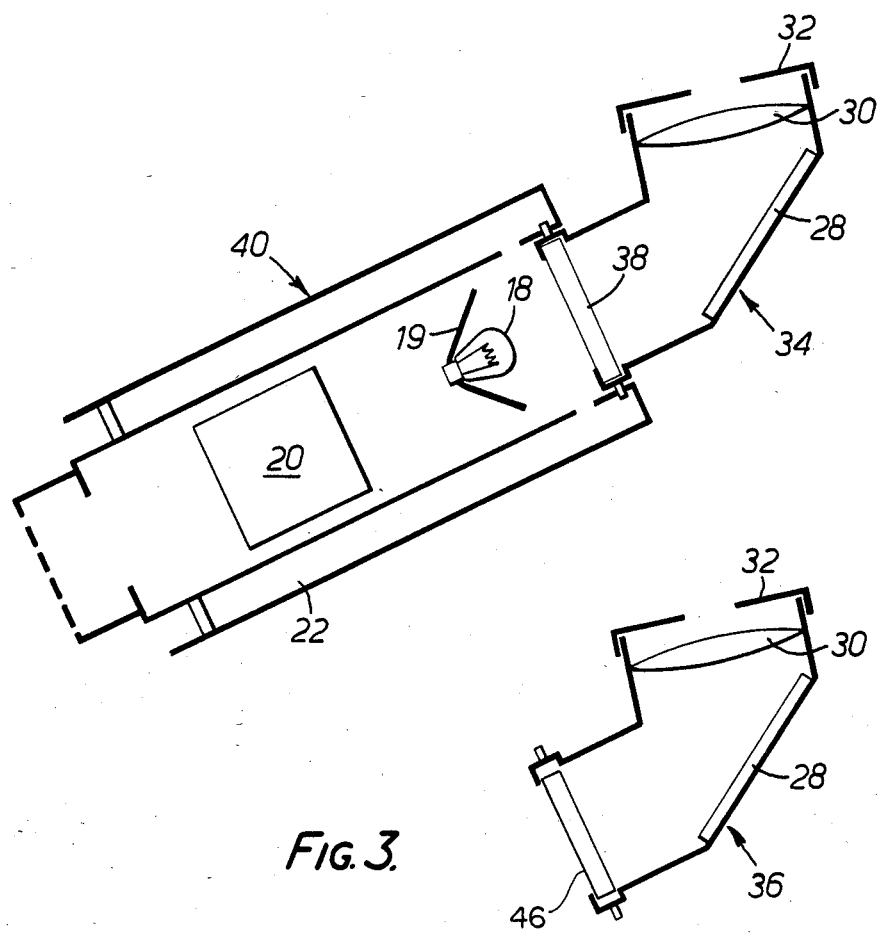
FIG. 3 is a diagrammatic section of an elevation of an alternative housing for use with a tele-diaphanography apparatus in accordance with the second aspect of the present invention.

In an alternative arrangement, and in accordance with a second embodiment of the invention, instead of using two separate housings for the visual examination and for recording the transilluminated image, a single housing as shown in FIG. 3 is used, the housing having two interchangeable angled extensions 34 and 36 which are selectively coupled, for example by use of a bayonet fitting, to the cylindrical casing of the housing 40. In this arrangement, the heat-absorbing filter 38 instead of being housed in the cylindrical casing is held at the inner end of the angled extension 34 which is fitted to the housing when a visual examination of the patient's breasts is to be made. The angled extension 36 which is used when a permanent record of the transilluminated image is to be made contains no infra-red absorber. In other respects the construction of the housing of FIG. 3 is the same as that of the housing of FIG. 2.

In order to facilitate examination of breasts of different sizes, the apparatus may be provided with a number of angled-extensions 34, 36 such as those described above, but having different diameters and different shapes, the operator selecting the angled-extension having dimensions most appropriate for the size and shape of the breast under examination.

Although the embodiments described above incorporate one or two housings only it should be understood that the present invention can also be used with an arrangement which includes additional housing which have the ability to use different band pass filters.

In order to further enhance the image quality and visual perception of the image, instead of generating a single image to be recorded with light of one spectral composition, it may be desirable to produce from one object at least two images generated with light of different spectral composition, typically by selectively incorporating in the housing for examining the tissue different band pass or step filters 46, and arranging for these different images to be processed by a computer 44 or microprocessor to produce a composite image by addition, subtraction ratio or other comparison of said images.

The apparatus of the present invention thus enables a thorough examination of the patient to be performed easily with no fear of causing discomfort to the patient by undue heating of the breast tissue. As the light source used for recording the image of the transilluminated tissue need only be switched on for a few milliseconds or less, there is no likelihood of burning the breast tissue while taking a permanent record of the transilluminated breast tissue.

I claim:

1. A tele-diaphanography apparatus suitable for transilluminating human or animal tissues, which apparatus comprises a first source of light of wavelength from 300 Nm to 2000 Nm, a first housing in which said first light source is mounted, a first light exit aperture in said first housing, a first means for directing onto the tissue to be examined transillumination light which is emitted by said first source of light through said first light exit aperture, a heat absorbing filter for absorbing infra-red radiation, said filter being located in the path of the light from said first light source to the tissues to be examined; a second source of light of wavelength from 300 Nm to 2000 Nm, a second housing in which said second light source is mounted, a second light exit aperture in said second housing, a second means for directing onto the tissues to be examined light which is emitted by said second source of light through said second exit aperture; power supply means for controlling the first and second light sources; means for connecting said first and second light sources to said power supply means; a light detector for detecting the light emitted from said second light source and transmitted through the transilluminated tissue being examined, said light detector adapted to be positioned in use on the opposite side of the tissue from said second source of light; a visual display unit connected to said light detector for displaying an image detected by said light detector; and recording means for recording the image detected by said light detector.

2. An apparatus as claimed in claim 1, wherein said light detector comprises a television camera including means sensitive to red and infra-red light.

3. An apparatus as claimed in claim 1, further comprising connecting means including an alpha-numeric generator and associated keyboard, by which said recording means and said visual display unit are connected to said light detector, said connecting means enabling data relating to the image being viewed and recorded to be transferred to and displayed on said visual display unit.

4. An apparatus as claimed in claim 1, further comprising a pseudo-color generator connected to said light detector for generating according to a chosen color scale a pseudo-colored image from the image recorded by said light detector.

5. An apparatus as claimed in claim 1, wherein said second means for directing includes selectively different filters so as to produce various images from light of different spectral composition, and said apparatus further includes a computer means for storing the images made with said different filters, said computer means being adapted to produce a processed image by means of the addition, subtraction, ratio or other comparison of said images.

6. An apparatus as claimed in claim 5, wherein said filters are bandpass filters.

7. An apparatus as claimed in claim 5, wherein said filters are step filters.

8. An apparatus as claimed in claim 1, wherein said recording means is a video-recorder.

9. An apparatus as claimed in claim 1, wherein said first and second means for directing each include a respective means, including a lens and a variable diaphragm, for assisting in obtaining optimal resolution of the image to be recorded, the light from the respective said light source being directable through the respective said means for assisting.

10. An apparatus as claimed in claim 1, wherein said first and second housings each include a respective fan for drawing air through the respective said housing thereby to cool the respective said housing.

11. An apparatus as claimed in claim 1, wherein said first and second housings are each connected by a respective flexible conduit to a fan which draws air through the respective said conduit and the respective said housing thereby to cool the respective said housing.

12. A tele-diaphanography apparatus suitable for transilluminating human or animal tissues, which apparatus comprises a source of light of wavelength from 300 Nm to 2000 Nm; a housing in which said light source is mounted; a light exit aperture in said housing; a first means, which is engageable with said housing, for directing onto the tissue to be examined transillumination light which is emitted by said light source through said light exit aperture; a heat absorbing filter for absorbing infra-red radiation, said filter being mounted in said first means for directing so that when said first means for directing is engaged with said housing said filter is located in the path of the light from said light source to the tissues to be examined; a second means, which is engageable with said housing, for directing onto the tissues to be examined transillumination light which is emitted by said light source through said light exit aperture, said first and second means for directing being selectively alternatively engageable with said housing so that light from said light source can be directed through either said first or said second means for directing as desired, power supply means for controlling said light source; means for connecting said light source to said power supply means, a light detector for detecting the light which is emitted from said light source, directed through said second means for directing and transmitted through the transilluminated tissue adapted to be examined, said light detector being positioned in use on the opposite side of the tissue from said light source; a visual display unit connected to said light detector for displaying an image detected by said light detector; and recording means for recording the image detected by said light detector.

13. An apparatus as claimed in claim 12, wherein said second means for directing includes selectively different filters so as to produce various images from light of different spectral composition, and said apparatus further includes a computer means for storing the images made with the different filters, said computer means being adapted to produce a processed image by means of the addition, subtraction, ratio or other comparison of said images.

14. An apparatus as claimed in claim 13, wherein said filters are bandpass filters.

15. An apparatus as claimed in claim 13, wherein said filters are step filters.

16. an apparatus as claimed in claim 12, wherein said first and second means for directing each include a respective means, including a lens and a variable diaphragm, for assisting in obtaining optimal resolution of the image to be recorded, the light from said light source beign directable through the respective said means for assisting.

17. An apparatus as claimed in claim 12, wherein said housing includes a fan for drawing air through said housing thereby to cool said housing.

18. An apparatus as claimed in claim 12, wherein said housing is connected by a flexible conduit to a fan which draws air through said conduit and said housing thereby to cool said housing.

* * * * *